(12) United States Patent
Hara et al.

(10) Patent No.: US 11,484,281 B2
(45) Date of Patent: Nov. 1, 2022

(54) RADIATION IMAGE IMAGING APPARATUS, ELECTRONIC DEVICE, WIRELESS COMMUNICATION SYSTEM, AND STORAGE MEDIUM

(71) Applicant: KONICA MINOLTA, INC., Tokyo (JP)

(72) Inventors: Kentaro Hara, Hino (JP); Naoki Hayashi, Higashimurayama (JP)

(73) Assignee: KONICA MINOLTA, INC., Tokyo (JP)

( * ) Notice: Subject to any disclaimer, the term of this patent is extended or adjusted under 35 U.S.C. 154(b) by 129 days.

(21) Appl. No.: 16/840,517

(22) Filed: Apr. 6, 2020

(65) Prior Publication Data
US 2020/0355630 A1 Nov. 12, 2020

(30) Foreign Application Priority Data

May 10, 2019 (JP) .............................. JP2019-089600
Oct. 2, 2019 (JP) .............................. JP2019-181807

(51) Int. Cl.
*A61B 6/00* (2006.01)
*G01N 23/04* (2018.01)
*H04W 88/02* (2009.01)

(52) U.S. Cl.
CPC ................ *A61B 6/566* (2013.01); *A61B 6/42* (2013.01); *A61B 6/4208* (2013.01);
(Continued)

(58) Field of Classification Search
CPC ....... A61B 6/42; A61B 6/4208; A61B 6/4233; A61B 6/4283; A61B 6/46; A61B 6/461;
(Continued)

(56) References Cited

U.S. PATENT DOCUMENTS 6,879,661 B2 * 4/2005 Tsuchino ............... A61B 6/548
378/92
7,250,608 B2 * 7/2007 Ozeki ................... G01T 1/2018
250/580

(Continued)

FOREIGN PATENT DOCUMENTS

JP 2017006427 A 1/2017

OTHER PUBLICATIONS

U.S. Appl. No. 16/684,226; First Named Inventor: Takanori Ando Title: "Image Display Control System, Image Display System, and Image Analysis Device"; filed Nov. 14, 2019.

*Primary Examiner* — Allen C. Ho
(74) *Attorney, Agent, or Firm* — Holtz, Holtz & Volek PC

(57) ABSTRACT

A radiation image imaging apparatus which generates an image from irradiated radiation, the radiation image imaging apparatus including: a communication unit which directly communicates by wireless communication with an information processing apparatus, which performs wireless communication, and receives installation setting information transmitted from the information processing apparatus to perform a predetermined setting at a time of an installation; and a hardware processor which performs the predetermined setting of the radiation image imaging apparatus in accordance with the installation setting information received by the communication unit.

18 Claims, 4 Drawing Sheets

(52) U.S. Cl.
CPC .......... *A61B 6/4233* (2013.01); *A61B 6/4283* (2013.01); *A61B 6/4452* (2013.01); *A61B 6/46* (2013.01); *A61B 6/461* (2013.01); *A61B 6/462* (2013.01); *A61B 6/465* (2013.01); *A61B 6/469* (2013.01); *A61B 6/54* (2013.01); *A61B 6/542* (2013.01); *A61B 6/545* (2013.01); *A61B 6/563* (2013.01); *G01N 23/04* (2013.01); *G01N 2223/304* (2013.01); *G01N 2223/306* (2013.01); *H04W 88/02* (2013.01)

(58) Field of Classification Search
CPC ......... A61B 6/462; A61B 6/465; A61B 6/467; A61B 6/469; A61B 6/54; A61B 6/542; A61B 6/545; A61B 6/56; A61B 6/563; A61B 6/566; A61B 6/44; A61B 6/4405; A61B 6/4411; A61B 6/4452
USPC ........ 378/62, 91, 98.8, 189–192; 250/370.09
See application file for complete search history.

(56) References Cited

U.S. PATENT DOCUMENTS

| | | | | |
|---|---|---|---|---|
| 7,365,337 B2* | | 4/2008 | Tsuchino | A61B 6/4488 250/370.09 |
| 7,382,859 B2* | | 6/2008 | Nokita | A61B 6/585 378/91 |
| 7,573,034 B2* | | 8/2009 | Heath | G03B 42/02 250/361 R |
| 7,732,779 B2* | | 6/2010 | Kito | G01T 7/00 250/370.09 |
| 7,777,193 B2* | | 8/2010 | Kito | G01T 7/00 250/370.09 |
| 7,844,031 B2* | | 11/2010 | Newman | A61B 6/467 378/114 |
| 7,991,119 B2* | | 8/2011 | Yoshida | G01T 1/00 378/114 |
| 8,080,802 B2* | | 12/2011 | Nishino | A61B 6/56 250/370.08 |
| 8,107,590 B2* | | 1/2012 | Nishino | G03B 42/04 378/62 |
| 8,130,909 B2* | | 3/2012 | Nishino | H04N 5/325 378/42 |
| 8,213,573 B2* | | 7/2012 | Liu | A61B 6/4405 378/62 |
| 8,229,202 B2* | | 7/2012 | Kito | A61B 6/00 378/114 |
| 8,546,777 B2* | | 10/2013 | Utsunomiya | A61B 6/56 250/580 |
| 8,654,926 B2* | | 2/2014 | Ohta | G01T 1/24 378/114 |
| 9,131,593 B2* | | 9/2015 | Arima | A61B 6/563 |
| 9,204,855 B2* | | 12/2015 | Tsubota | H04W 76/10 |
| 9,521,986 B2* | | 12/2016 | Ozawa | A61B 6/4233 |
| 9,538,969 B2* | | 1/2017 | Nishii | A61B 6/542 |
| 9,538,978 B2* | | 1/2017 | Makino | A61B 6/563 |
| 9,757,086 B2* | | 9/2017 | Tezuka | A61B 6/56 |
| 9,788,809 B2* | | 10/2017 | Hiroike | A61B 6/54 |
| 9,943,284 B2 | | 4/2018 | Tamura et al. | |
| 10,058,297 B2* | | 8/2018 | Park | A61B 6/4208 |
| 10,251,619 B2* | | 4/2019 | Park | H04W 60/04 |
| 10,368,826 B2* | | 8/2019 | Tamura | H05G 1/34 |
| 10,433,809 B2* | | 10/2019 | Park | A61B 6/563 |
| 10,492,750 B2* | | 12/2019 | Tajima | A61B 6/12 |
| 10,548,554 B2* | | 2/2020 | Arima | A61B 6/465 |
| 10,605,747 B2* | | 3/2020 | Ubukata | G01T 1/17 |
| 10,708,497 B2* | | 7/2020 | Ohguri | A61B 6/4233 |
| 10,722,198 B2* | | 7/2020 | Wirth | G16H 10/65 |
| 10,736,597 B2* | | 8/2020 | Yachi | A61B 6/548 |
| 10,754,046 B2* | | 8/2020 | Kosuge | A61B 6/54 |
| 10,758,196 B2* | | 9/2020 | Kosuge | G16H 30/20 |
| 10,786,221 B2* | | 9/2020 | Mako | H04N 7/56 |
| 10,842,459 B2* | | 11/2020 | Isogai | A61B 6/463 |
| 10,849,577 B2* | | 12/2020 | Okumura | A61B 6/486 |
| 10,853,450 B2* | | 12/2020 | Abe | A61B 6/465 |
| 10,856,833 B2* | | 12/2020 | Niwa | A61B 6/4452 |
| 10,856,834 B2* | | 12/2020 | Uchiyama | A61B 6/4208 |
| 10,888,295 B2* | | 1/2021 | Kawamura | A61B 6/544 |
| 10,888,298 B2* | | 1/2021 | Takekoshi | A61B 6/548 |
| 10,925,558 B2* | | 2/2021 | Kim | A61B 6/00 |
| 10,925,561 B2* | | 2/2021 | Snow | A61B 6/46 |
| 10,932,747 B2* | | 3/2021 | Hara | A61B 6/4233 |
| 10,939,890 B2* | | 3/2021 | Kuwata | A61B 6/542 |
| 10,952,697 B2* | | 3/2021 | Lalena | A61B 6/586 |
| 10,959,690 B2* | | 3/2021 | Wojcik | A61B 6/4233 |
| 10,959,697 B2* | | 3/2021 | Richard | H04N 5/32 |
| 10,966,673 B2* | | 4/2021 | Park | A61B 6/4208 |
| 11,134,205 B2* | | 9/2021 | Kuwata | H04N 5/32 |
| 11,172,898 B2* | | 11/2021 | Fukasawa | A61B 6/54 |
| 11,219,114 B2* | | 1/2022 | Kuwata | G01N 23/04 |
| 11,357,459 B2* | | 6/2022 | Ishioka | A61B 6/56 |
| 2012/0239431 A1 | | 9/2012 | Hayashi | |

* cited by examiner

RADIATION IMAGE IMAGING APPARATUS, ELECTRONIC DEVICE, WIRELESS COMMUNICATION SYSTEM, AND STORAGE MEDIUM

CROSS-REFERENCE TO RELATED APPLICATIONS

The entire disclosure of Japanese Patent Application No. 2019-089600 filed on May 10, 2019 and Japanese Patent Application No. 2019-181807 filed on Oct. 2, 2019 are incorporated herein by reference in its entirety.

BACKGROUND

Technological Field

The present invention relates to a radiation image imaging apparatus, an electronic device, a wireless communication system, and a storage medium.

Description of the Related Art

In recent years, the use of X-ray image imaging apparatus (Digital Radiography) systems in small-scale sites such as clinics and healthcare sites in developing countries has been expanding.

As a DR system, a DR system in which a plurality of devices are connected by wireless communication is known, but as the use environment expands, a technology for enabling communication between devices even when the state of wireless communication is poor has been developed. For example, JP 2017-6427A proposes a technique that enables an imaging apparatus to have a function as a parent device of an access point and to be a relay device from another imaging apparatus (child device).

In general, when newly installing an imaging apparatus, setting work is performed by a serviceman having specialized knowledge in order to cope with various network environments and to implement complicated and troublesome installation procedures.

However, in clinics and developing countries, due to the small scale of the system, the elements that require conventional complex installation procedures are limited. In addition, it is considered that the time required for the site visit is larger than the work time for the installation setting, such as an increase in the number of deployment facilities and installation in a frontier area. Furthermore, it takes a long time and effort to operate if a specialist serviceman must be called in the event of a failure or the like.

For this reason, there is a rising demand that even a person who does not have specialized knowledge can easily set the setting at the time of installation of the imaging apparatus.

SUMMARY

It is an object of the present invention to provide a radiation image imaging apparatus, an electronic device, a wireless communication system, and a storage medium that enable a person who does not have specialized knowledge to easily perform setting at the time of installation.

To achieve at least one of the abovementioned objects, according to an aspect of the present invention, a radiation image imaging apparatus reflecting one aspect of the present invention generates an image from irradiated radiation, the radiation image imaging apparatus including: a communication unit which directly communicates by wireless communication with an information processing apparatus which performs wireless communication, and receives installation setting information transmitted from the information processing apparatus to perform predetermined setting at the time of installation; and a hardware processor which performs setting of the radiation image imaging apparatus in accordance with the installation setting information received by the communication unit.

According to another aspect of the present invention, an electronic device, which is used when performing predetermined setting at the time of installation, includes: a communication unit which directly communicates by wireless communication with an information processing apparatus which performs wireless communication, and receives installation setting information transmitted from the information processing apparatus to perform predetermined setting at the time of installation; and a hardware processor which performs setting of the electronic device in accordance with the installation setting information received by the communication unit.

According to another aspect of the present invention, a wireless communication system includes: a radiation image imaging apparatus which generates an image from irradiated radiation; and an information processing apparatus connectable to the radiation image imaging apparatus by wireless communication, wherein, the radiation image imaging apparatus includes, a communication unit which directly communicates by wireless communication with the information processing apparatus, and receives installation setting information transmitted from the information processing apparatus to perform predetermined setting at the time of installation; and a hardware processor which performs setting of the radiation image imaging apparatus in accordance with the installation setting information received by the communication unit.

According to another aspect of the present invention a non-transitory computer-readable storage medium storing a program for causing a computer of a radiation image imaging apparatus which generates an image from irradiated radiation to perform the following: communicating directly by wireless communication with an information processing apparatus which performs wireless communication, and receiving installation setting information transmitted from the information processing apparatus to perform predetermined setting at the time of installation; and performing setting of the radiation image imaging apparatus in accordance with the installation setting information received in the communicating.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein.

DETAILED DESCRIPTION OF THE EMBODIMENTS

Hereinafter, one or more embodiments of the present invention will be described with reference to the drawings. However, the scope of the invention is not limited to the disclosed embodiments and the illustrated drawings.

[Radiation Detection System]

Figure 1:
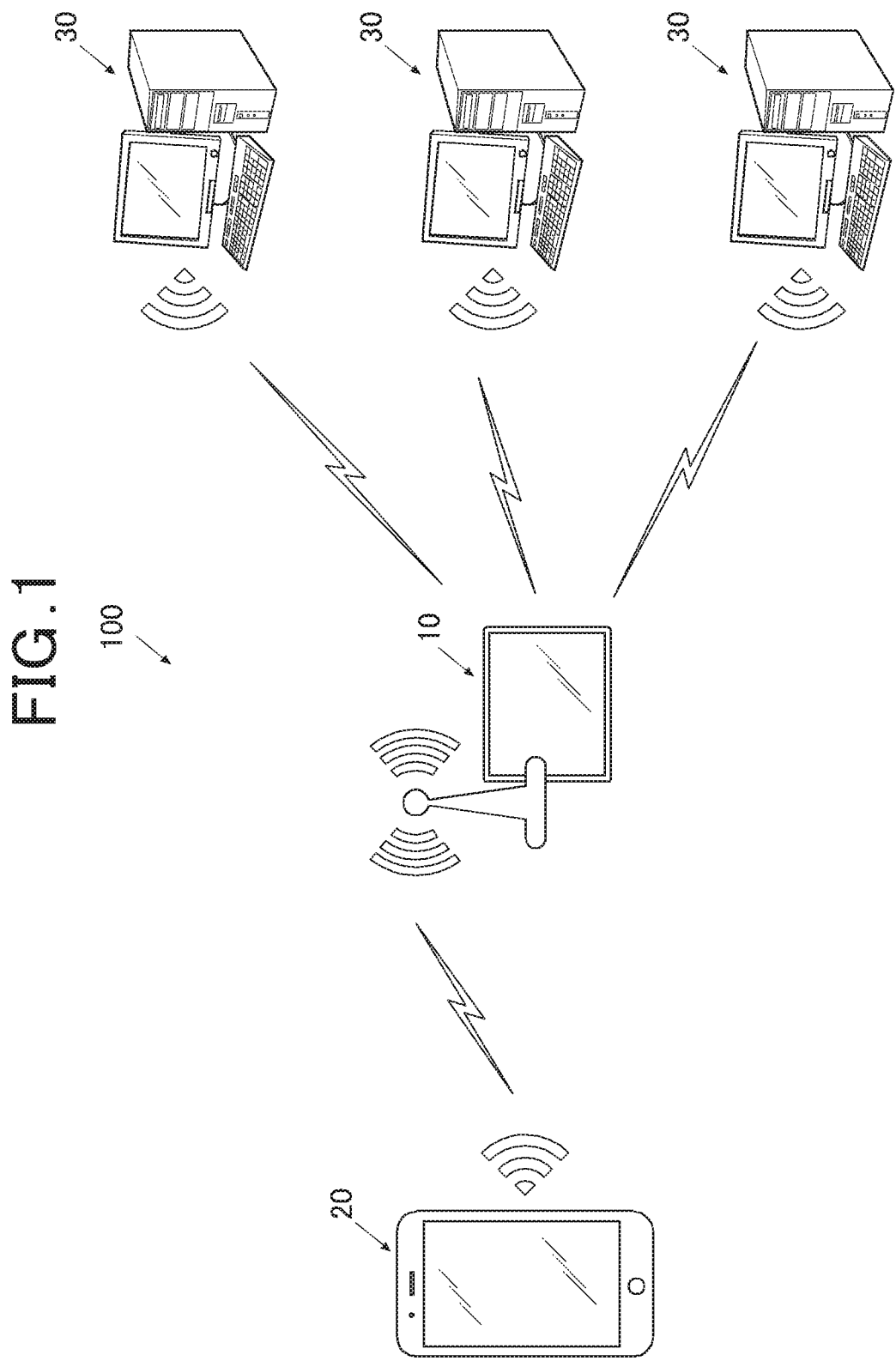
FIG. 1 is a diagram showing a schematic configuration of a radiation detection system.

First, an outline of a radiation detection system 100 as a wireless communication system of the present embodiment will be described. FIG. 1 is a block diagram showing a schematic configuration of a radiation detection system 100.

As shown in FIG. 1, the radiation detection system 100 includes a radiation image imaging apparatus 10 (hereinafter simply referred to as imaging apparatus), a terminal apparatus 20 as an information processing apparatus, and a console 30.

The imaging apparatus 10 is, for example, a panel-shaped device that generates image data of a radiation image based on radiation such as X-rays generated and irradiated by an irradiation apparatus (not shown).

The terminal apparatus 20 is, for example, a portable terminal apparatus used by a user who performs a setting (hereinafter, sometimes referred to as "installation setting") at the time of installation of the imaging apparatus 10.

In the present embodiment, the imaging apparatus 10 has an access point function capable of operating as a parent device, the terminal apparatus 20 can operate as a child device, and the imaging apparatus 10 and the terminal apparatus 20 can perform direct wireless communication by, for example, Wi-Fi (registered trademark). In addition, the imaging apparatus 10 and the terminal apparatus 20 can directly perform wireless communication by Bluetooth (registered trademark). The terminal apparatus 20 may have a wired communication function, and may be connected to the imaging apparatus 10 via a device which converts wired communication to wireless communication. The terminal apparatus 20 makes it possible to perform the installation setting of the imaging apparatus 10.

The console 30 is configured by a personal computer (Personal Computer), a dedicated device, or the like, and the console 30 is a device that allows a user or the like to instruct the imaging apparatus 10 to set various imaging conditions (imaging site, imaging directions, length of time of irradiation, and the like), start/end of imaging, and the like.

[Radiation Image Imaging Apparatus]

Figure 2:
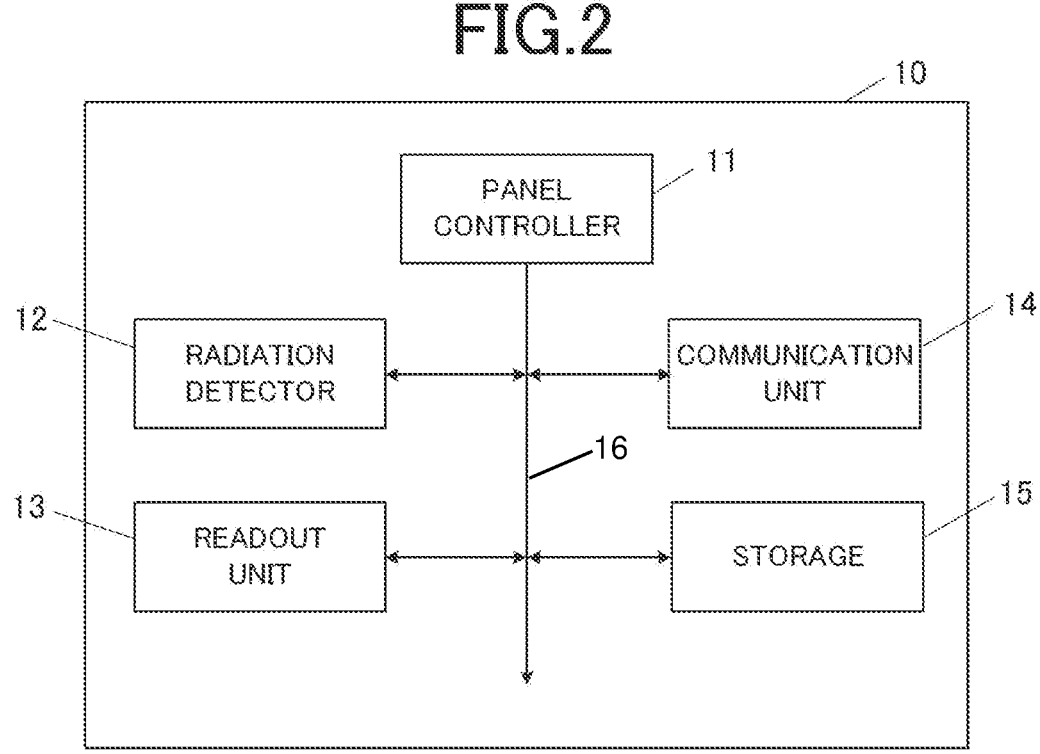
FIG. 2 is a block diagram showing a configuration of a radiation image imaging apparatus.

Next, the details of the imaging apparatus 10 will be described. FIG. 2 is a block diagram showing a configuration of the imaging apparatus 10.

As shown in FIG. 2, the imaging apparatus 10 includes a panel controller (setting unit, determination unit, mode setting unit) 11, a radiation detector 12, a readout unit 13, a communication unit 14, a storage 15, and the like, and the units 11 to 15 are connected by a bus 16.

The panel controller 11 is configured to collectively control the operations of the respective units of the imaging apparatus 10 by a CPU (Central Processing Unit), a RAM (Random Access Memory), and the like.

More specifically, the panel controller 11 reads out various processing programs stored in the storage 15, deploys the programs in the RAM, and executes installation setting processing of the imaging apparatus 10 in accordance with the processing program, upon receipt of an instruction signal from the terminal apparatus 20.

After the installation setting of the imaging apparatus 10 is performed, the panel controller 11 reads out various processing programs stored in the storage 15, deploys the programs in the RAM, and performs processing such as generating image data of a radiation image in accordance with the processing program, triggered by the power switch being turned on, a predetermined control signal being received from the irradiation apparatus (not shown) or the console 30, radiation being received from the irradiation apparatus, and the like.

The radiation detector 12 may be any unit as long as it has a substrate in which a plurality of pixels are two-dimensionally arrayed. Each of the plurality of pixels has a radiation detection element for directly or indirectly generating a charge in an amount corresponding to a dose of radiation, and a switch element provided between each radiation detection element and a wiring and capable of switching to an on state in which electricity can be supplied between the radiation detection element and the wiring or an off state in which electricity cannot be supplied. Conventionally known ones can be used.

That is, the imaging apparatus 10 may be a so-called indirect type which includes a scintillator and the imaging apparatus 10 detects light emitted by the scintillator receiving radiation. Alternatively, the imaging apparatus 10 may be a so-called direct type in which radiation is directly detected without passing through a scintillator or the like.

The readout unit 13 may be configured so as to be able to read out the amount of charge accumulated in each of the plurality of radiation detection elements as a signal value, and a conventionally known one can be used.

The communication unit 14 includes a wireless communication interface, and transmits and receives data to and from external devices (e.g., terminal apparatuses 20) connected via communication networks such as LAN (Local Area Network), WAN (Wide Area Network), and the Internet.

The storage 15 is configured by an HDD (Hard Disk Drive), a semiconductor memory, and the like, and stores various processing programs including various image processing programs, parameters and files required to execute the programs, and the like.

Specifically, the storage 15 stores installation setting information indicating the installation state of the imaging apparatus 10.

The installation setting information includes one or a plurality of items determined in advance, and for each item, it is possible to judge whether the setting of the item is finished or not. This is realized, for example, by using a flag such as "finished flag"/"not-finished flag", by inputting a specific value, or by judging whether or not all the specific item groups have been set. It should be noted that the present embodiment is not limited as long as it is possible to determine that the setting is finished.

Specifically, the items included in the installation setting information include, for example, "IP address", "display name of the panel icon displayed on the console", "background color of panel icon displayed on the console", "enable/disable of auto power ON/OFF function", "wireless LAN operation setting (parent device/child device)" "wireless LAN child device setting (SSID/passphrase)", "wireless LAN parent device setting (SSID/passphrase/wireless channel)", "mode switching button setting (memory imaging valid/invalid, etc.)", "correction data for gain correction and defect correction (including correction coefficient for correcting individual differences of the panel (for example, correction coefficient for gain correction and defect correction)", "imaging mode setting (linkage/non-linkage)", "license information (license information of panel itself, type of license related to imaging, expiration term)", "restriction setting 1 (upper limit of the number of times of irradiation, upper limit of the irradiation amount, alert output necessity setting when the upper limit is exceeded), and "restriction setting 2 (threshold of charge remaining amount, operation setting when the threshold value is exceeded), "display color of the display included in the panel itself", "information of the assigned console (PC name, console software version, network ID)", "encryption setting (type of encryption/decryption, encryption key, certificate) at the time of data communication", "setting of the alert output necessity when away from the place of use, the place of installation, or the set place (for example, imaging room)", and "power saving mode".

Note that the "display name of the panel icon displayed on the console" is stored in the panel (imaging apparatus) for the same display when the panel (imaging apparatus) is shared by a plurality of consoles. The "background color of a panel icon to be displayed on the console" is also stored in the panel (imaging apparatus) for the same display when the panel (imaging apparatus) is shared by a plurality of consoles.

The "display name of the panel icon displayed on the console" and the "background color of the panel icon to be displayed on the console" may be recorded on the console or may be stored on each of the console panels, in addition to the configuration recorded on the panel as described above.

The items included in the above installation setting information can be grouped into, for example, "items related to communication setting", "items caused by facility installation environment", "items related to imaging", and "setting items related to operability, safety (security), maintenance, etc.".

The method of grouping is not limited to that exemplified here, and may be appropriately grouped according to the facility or the like.

The "items related to the communication setting" include "IP address", "wireless LAN operation setting (parent device/child device)", "wireless LAN child device setting (SSID/path phrase)", "wireless LAN parent device setting (SSID/path phrase/wireless channel)", and "information of the assigned console (PC name, console software version, network ID)".

"Items attributable to facilities installation environments" include "license information (whether there is license of panel itself, the type of license related to imaging, and the expiration term)", "setting of alert output necessity when separated from the use place, installation place, and set place such as the imaging room", and "validity/invalidity of the auto power ON/OFF function".

The "items related to imaging" include "imaging mode setting (linkage/non-linkage)", "correction data for gain correction and defect correction (including correction coefficients for correcting individual differences of panels (for example, correction coefficients for gain correction and defect correction)", and "mode switching button setting (memory imaging valid/invalid, etc.)".

"Setting items related to operability, safety (security), maintenance, etc." include "display name of the panel icon displayed on the console", "background color of panel icon displayed on the console", "restriction setting 1 (upper limit of number of times of irradiation, upper limit of irradiation amount, and setting of necessity of alert output when the upper limit is exceeded)", "restriction setting 2 (threshold of remaining charge, operation setting when the threshold is exceeded)", "display color of the display included in the panel itself", "encryption setting (type of encryption/decryption, encryption key, certificate) at the time of data communication", and "power saving mode".

The panel controller 11 of the imaging apparatus 10 configured as described above performs the following operations in accordance with the processing program stored in the storage 15.

That is, the installation setting of the imaging apparatus 10 is performed in accordance with an instruction signal from the terminal apparatus 20.

The panel controller 11 has a function of switching on and off the switching element of the radiation detector 12. The panel controller 11 has a function of generating image data of a radiation image based on the signal value read by the readout unit 13.

[Terminal Apparatus]

Figure 3:
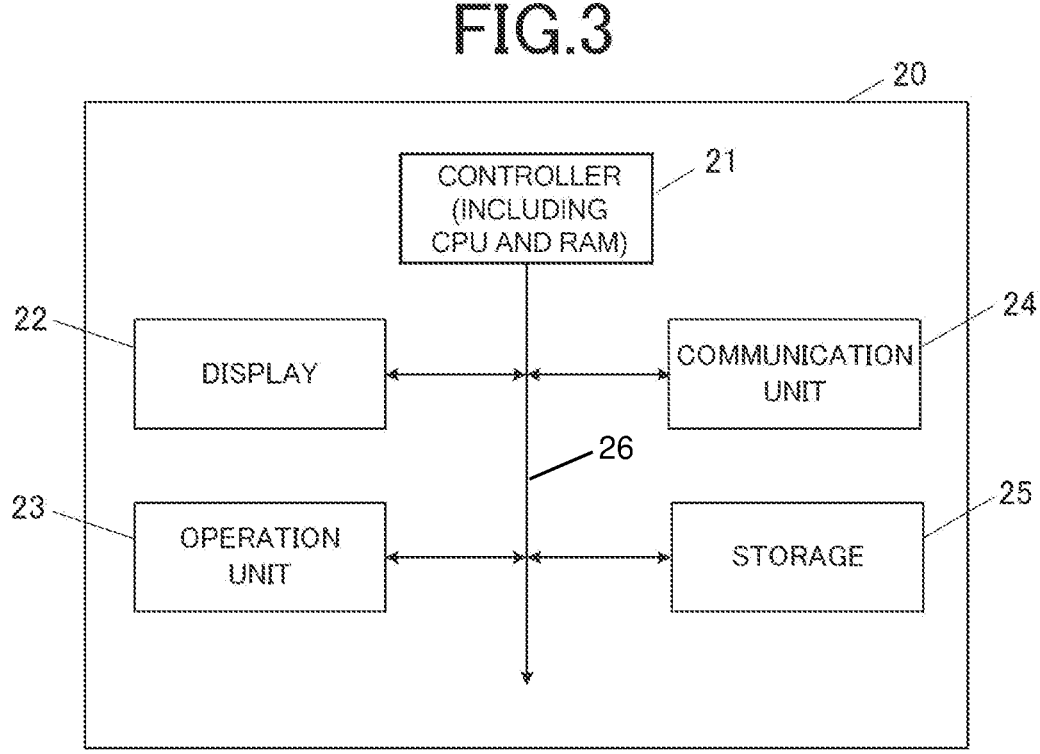
FIG. 3 is a block diagram showing a configuration of a terminal apparatus.

Next, details of the terminal apparatus 20 will be described. FIG. 3 is a block diagram showing the configuration of the terminal apparatus 20.

As shown in FIG. 3, the terminal apparatus 20 includes a controller 21, a display 22, an operation unit 23, a communication unit 24, a storage 25, and the like, and the respective units 21 to 25 are connected by a bus 26. Electric power is supplied from a built-in battery (not shown) to the respective units 21 to 25.

As the terminal apparatus 20, it is preferable to use a mobile phone, a smart phone, a tablet terminal, a notebook PC, a head mounted display, or the like, which is configured to be carried or worn by the user.

The controller 21 is configured to collectively control the operation of each unit of the terminal apparatus 20 by a CPU, a RAM, or the like.

Specifically, various display signals are transmitted to the display 22 by reading and executing the web application program stored in the storage 25 in accordance with the operation signal input from the operation unit 23.

The display 22 includes monitors such as Liquid Crystal Display, and displays various screens in accordance with instructions of display signals inputted from the controller 21.

Specifically, the display 22 can display, for example, a setting screen for installation setting of the imaging apparatus 10.

The operation unit 23 is configured to include a pointing device such as a keyboard or a mouse provided with various keys, or a touch panel laminated on the display 22, and outputs to the controller 21 an operation signal input in accordance with a position of a key operation on the keyboard, a mouse operation, or a touch operation on the touch panel.

The communication unit 24 is configured by a network interface or the like, and transmits and receives data or the like to and from an external device such as the imaging apparatus 10 or the like connected via a communication network such as LAN, WAN, or the Internet.

The controller 21 of the terminal apparatus 20 configured as described above displays, for example, a setting screen for setting the installation setting of the imaging apparatus 10 on the display 22.

In addition, the controller 21 causes the communication unit 24 to transmit an instruction signal to the imaging apparatus 10 when a predetermined instruction operation is performed in a state where the setting screen is displayed.

[Operation of Radiation Detection System]

Next, an installation setting process of the imaging apparatus 10 constituting the radiation detection system 100 will be described.

Figure 4:
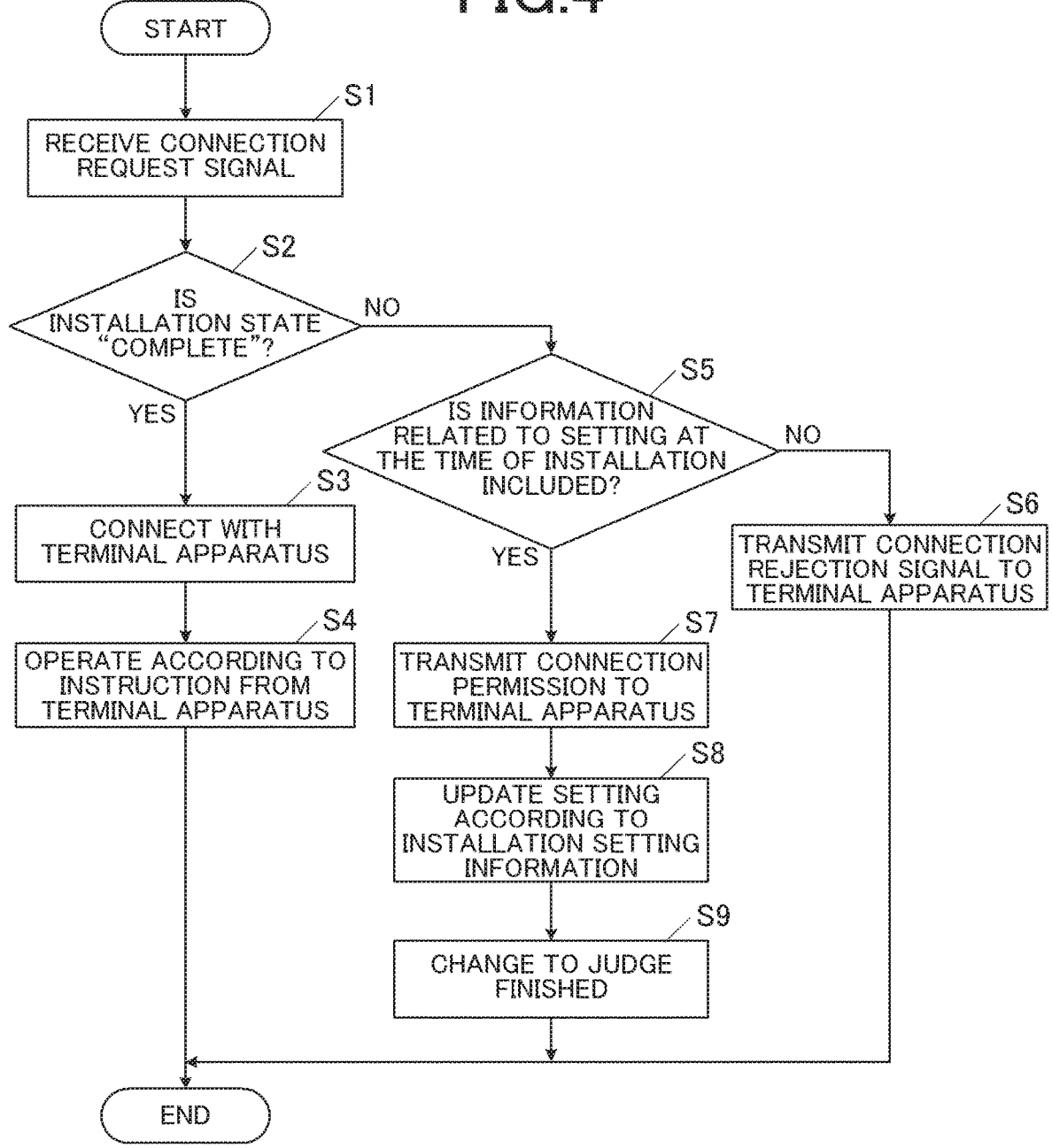
FIG. 4 is a flowchart showing a setting operation at the time of installation of the imaging apparatus.

The radiation detection system 100 according to the present embodiment enables installation setting of the imaging apparatus 10 in a facility or the like by using the terminal apparatus 20. FIG. 4 is a flowchart showing an installation setting process of the imaging apparatus 10.

It is to be noted that, as a premise, in the initial setting state at the time of factory shipment, the imaging apparatus 10 is in a state in which a predetermined operation can be performed. That is, in the initialization, SSID and passwords for operating as parent devices (access points) in the wireless communication are set in the imaging apparatus 10. Such setting may allow connection to the Internet.

When the controller 21 of the terminal apparatus 20 transmits a connection request signal to the imaging apparatus 10 in accordance with a user operation through the operation unit 23, the panel controller 11 of the imaging apparatus 10 receives the connection request signal (step S1).

Next, the panel controller 11 of the imaging apparatus 10 confirms the installation state of the imaging apparatus 10, and determines whether or not the installation state is "completed" (step S2).

Specifically, the controller 21 refers to the installation setting information of the storage 15, and determines whether or not the setting of all the items has been completed. That is, when all the items are judged to be "finished", the installation state is judged to be "completed", and when there is an item judged to be "not finished", the installation state is judged to be "not completed".

When the items included in the installation setting information are grouped, and when all the items of the predetermined set are determined to be "finished", the installation state may be determined to be "completed".

Next, when the installation state is "completed" (step S2: YES), the panel controller 11 transmits connection permission to the terminal apparatus 20 to perform connection (step S3), and performs a predetermined operation in accordance with an instruction from the terminal apparatus 20 (step S4). For example, an operation such as imaging start is performed.

On the other hand, when the installation state is "incomplete" (step S2: NO), the panel controller 11 determines whether or not the connection request signal from the terminal apparatus 20 includes information related to installation (step S5), and when information related to installation is not included (step S5: NO), the panel controller 11 transmits a connection rejection signal to the terminal apparatus 20 (step S6).

For example, when information related to imaging is included, it is determined that information related to installation is not included. For this reason, it is possible to avoid a situation in which imaging or the like is started in a state in which the installation setting is not completed.

In this regard, in recent years, there has been an increase in the number of cases in which a doctor or the like carries only the imaging apparatus 10 and goes to the rounds. At this time, it is often not checked in advance whether the imaging apparatus 10 can perform imaging, and if the imaging apparatus 10 is carried without noticing that the installation setting of the imaging apparatus 10 is not completed, there is a possibility that an error in imaging occurs due to the installation setting being incomplete. According to the processing of the above-mentioned steps S2 (NO), S5 (NO), and S6, since the imaging apparatus 10 in which the installation setting is not completed cannot communicate, the erroneous imaging can be prevented, and the user can identify that the installation setting of the target imaging apparatus 10 is not completed.

Note that the "installation-related information" may be any information as long as it indicates information related to installation of the imaging apparatus 10, and may be, for example, the entire installation setting information, or may be only a part of the installation setting information.

On the other hand, when the information on the installation is included (step S5: YES), the panel controller 11 transmits the connection permission to the terminal apparatus 20 to perform the connection (step S7), and performs the setting of the imaging apparatus 10 according to the received installation setting information (step S8).

Next, the panel controller 11 makes a change to judge "finished" for the item set in step S8 (step S9), and ends the present process.

After the installation state is "completed", the imaging apparatus 10 is set to a mode operating as a parent device or a mode operating as a child device for another parent device in accordance with the installation setting information ("wireless LAN operation setting (parent device/child device)").

The mode is not limited to the above example, and may be set to, for example, a mode in which wireless communication is invalid.

When the power supply of the imaging apparatus 10 and/or the terminal apparatus 20 is turned off in a state in which the installation state is "incomplete", the imaging apparatus 10 may return to an initial setting state (a state at the time of factory shipment). That is, the content of the item included in the installation setting information returns to the initial setting state. For example, when the communication of the terminal apparatus 20 is disconnected, the state returns to the initial setting state.

In addition, the panel controller 11 may be configured to determine the terminal apparatus 20 during the installation setting process, and not to permit communication from another terminal apparatus 20 during the installation setting process. In this case, since the imaging apparatus 10 in which the installation setting is not completed cannot communicate with the other terminal apparatuses 20, it is possible to prevent erroneous imaging, and it is possible for the user to identify that the installation setting of the target imaging apparatus 10 is not completed.

When the installation setting information is transmitted while the installation state is "completed", the panel controller 11 may notify that the installation state is "completed".

The panel controller 11 may notify that the installation state is "completed" at the point in time when the installation state is "completed", or may notify that the processing is interrupted when the processing is interrupted while the installation state is still "incomplete".

As a notification method, for example, a message may be displayed on the display 22 of the terminal apparatus 20, or sound or light may be generated from the imaging apparatus 10.

Effects of Embodiments

As described above, according to the present exemplary embodiment, the imaging apparatus 10 for detecting the irradiated radiation is provided with an access point function operable as a parent device in wireless communication, includes a communication unit 14 which performs wireless communication directly with the terminal apparatus 20 operable as a child device in wireless communication, and receives the installation setting information transmitted from the terminal apparatus 20 for performing a predetermined setting at the time of installation, and a panel controller 11 for performing the setting of the imaging apparatus 10 according to the installation setting information received by the communication unit 14.

Therefore, installation setting of the imaging apparatus 10 in a facility or the like can be performed only by the imaging apparatus 10 and the terminal apparatus 20.

Therefore, even a person who does not have specialized knowledge can easily perform installation setting.

Further, according to the present embodiment, when the information is received from the terminal apparatus 20 by the communication unit 14, the panel controller 11 determines whether or not the installation setting is completed.

Specifically, when the setting of all the predetermined items is finished, the panel controller 11 determines that the installation setting is completed.

For this reason, it is possible to reliably perform the installation setting.

Further, according to this embodiment, when it is determined that the installation setting is not completed, the panel controller 11 determines whether or not the information received from the terminal apparatus 20 is information about the installation setting of the imaging apparatus 10. When it is determined that it is not information about the installation setting, the terminal apparatus 20 does not allow the wireless connection.

Therefore, the imaging apparatus 10 in which installation setting is not completed cannot communicate with other instructions, and erroneous imaging before completion of the installation setting can be prevented. Further, by rejecting the other instructions until the installation setting is completed, the installation setting can be reliably performed. In addition, the user can identify that the installation setting of the target imaging apparatus 10 is not completed.

Further, according to this embodiment, when it is determined that the installation setting is not completed, the panel controller 11 determines whether or not the terminal apparatus 20 which transmitted the information is the device executing the setting of the imaging apparatus 10. If it is determined that it is not the device that is executing the setting of the imaging apparatus 10, the wireless connection with the device is not permitted.

Therefore, the imaging apparatus 10 in which the installation setting is not completed cannot communicate with an instruction from another apparatus, and erroneous imaging before completion of the installation setting can be prevented. Further, by rejecting an instruction from another apparatus until the installation setting is completed, the installation setting can be surely performed. In addition, the user can identify that the installation setting of the target imaging apparatus 10 is not completed.

In addition, according to the present embodiment, after the installation setting is completed, the panel controller 11 sets the operation mode of the radiation image imaging apparatus 10 to one of a mode operating as a parent device, a mode operating as a child device with respect to another parent device, and a mode in which wireless communication is invalid in accordance with the installation setting information.

Therefore, the radiation image imaging apparatus 10 can be used efficiently in operation.

The embodiment to which the present invention can be applied is not limited to the embodiment described above, and can be appropriately changed within a range not deviating from the scope of the present invention.

Figure 5:
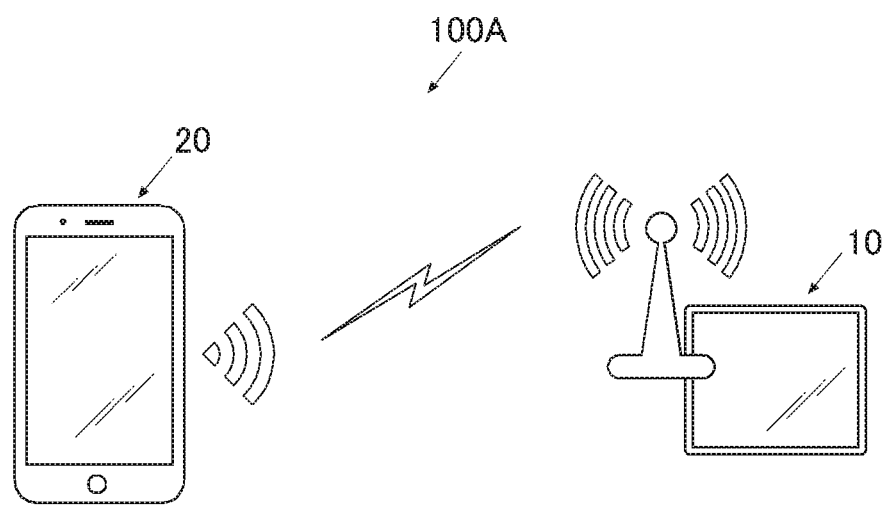
FIG. 5 is a diagram showing a schematic configuration of a radiation detection system of another embodiment.

For example, in the above embodiment, the terminal apparatus 20 is used only for the installation setting of the imaging apparatus 10, but as shown in FIG. 5, the radiation detection system 100A configured by the imaging apparatus 10 and the terminal apparatus 20 may be configured such that the terminal apparatus 20 is used for the installation setting and functions as a console after the setting of the installation is completed.

Further, in the above embodiment, the case where the installation setting of the radiation image imaging apparatus 10 is performed has been described as an example, but the installation setting of an electronic device such as a console 30 may be performed in addition to the radiation image imaging apparatus 10.

Although embodiments of the present invention have been described and illustrated in detail, the disclosed embodiments are made for purposes of illustration and example only and not limitation. The scope of the present invention should be interpreted by terms of the appended claims.

What is claimed is:

1. A radiation image imaging apparatus that generates an image from irradiated radiation, the radiation image imaging apparatus comprising:
   a communication interface that directly communicates by wireless communication with an information processing apparatus, wherein the communication interface receives installation setting information transmitted from the information processing apparatus to perform a predetermined setting of the radiation image imaging apparatus at a time of an installation of the radiation image imaging apparatus; and
   a hardware processor that performs the predetermined setting of the radiation image imaging apparatus at the time of the installation of the radiation image imaging apparatus in accordance with the installation setting information received by the communication interface, wherein:
   the hardware processor judges whether the predetermined setting of the radiation image imaging apparatus at the time of the installation of the radiation image imaging apparatus is completed when information is received from the information processing apparatus by the communication interface, and
   the information processing apparatus comprises a hardware processor and a communication interface.

2. The radiation image imaging apparatus according to claim 1, wherein the hardware processor of the radiation image imaging apparatus judges that the predetermined setting of the radiation image imaging apparatus at the time of the installation of the radiation image imaging apparatus is complete when a setting of all predetermined items is finished.

3. The radiation image imaging apparatus according to claim 1, wherein, when it is judged that the predetermined setting of the radiation image imaging apparatus at the time of the installation of the radiation image imaging apparatus is not completed, the hardware processor of the radiation image imaging apparatus judges whether the information received from the information processing apparatus is installation-related information related to the predetermined setting of the radiation image imaging apparatus at the time of the installation of the radiation image imaging apparatus, and when it is judged that the information is not the installation-related information, a wireless connection with the information processing apparatus is not permitted.

4. The radiation image imaging apparatus according to claim 1, wherein, when it is judged that the predetermined setting of the radiation image imaging apparatus at the time of the installation of the radiation image imaging apparatus is not completed, the hardware processor of the radiation image imaging apparatus judges whether the information processing apparatus, which transmitted the information, is a device in which the predetermined setting of the radiation image imaging apparatus at the time of the installation of the radiation image imaging apparatus is being executed, and when it is judged that the information processing apparatus is not the device in which the predetermined setting of the radiation image imaging apparatus at the time of the installation of the radiation image imaging apparatus is being executed, a wireless connection with the information processing apparatus is not permitted.

5. The radiation image imaging apparatus according to claim 1, wherein the radiation image imaging apparatus is provided with an access point function, whereby the radiation image imaging apparatus is operable as a parent device in wireless communication, and the information processing apparatus is operable as a child device in wireless communication with the radiation image imaging apparatus operating as the parent device.

6. The radiation image imaging apparatus according to claim 5, wherein, after the predetermined setting of the radiation image imaging apparatus at the time of the installation of the radiation image imaging apparatus is completed, the hardware processor sets an operation mode of the radiation image imaging apparatus to one of a mode operating as the parent device, a mode operating as a child device with respect to another parent device, or a mode in which wireless communication is invalid according to the installation setting information transmitted from the information processing apparatus.

7. An electronic device, comprising:
a communication interface that directly communicates by wireless communication with an information processing apparatus, wherein the communication interface receives installation setting information transmitted from the information processing apparatus to perform a predetermined setting of the electronic device at a time of an installation of the electronic device; and
a hardware processor that performs the predetermined setting of the electronic device at the time of the installation of the electronic device in accordance with the installation setting information received by the communication interface,
wherein:
the hardware processor judges whether the predetermined setting of the electronic device at the time of the installation of the electronic device is completed when information is received from the information processing apparatus by the communication interface, and
the information processing apparatus comprises a hardware processor and a communication interface.

8. A wireless communication system comprising:
a radiation image imaging apparatus that generates an image from irradiated radiation; and
an information processing apparatus connectable to the radiation image imaging apparatus by wireless communication,
wherein the radiation image imaging apparatus includes:
a communication interface that directly communicates by wireless communication with the information processing apparatus, and receives installation setting information transmitted from the information processing apparatus to perform a predetermined setting of the radiation image imaging apparatus at a time of an installation of the radiation image imaging apparatus; and
a hardware processor that performs the predetermined setting of the radiation image imaging apparatus at the time of the installation of the radiation image imaging apparatus in accordance with the installation setting information received by the communication interface,
wherein the hardware processor judges whether the predetermined setting of the radiation image imaging apparatus at the time of the installation of the radiation image imaging apparatus is completed when information is received from the information processing apparatus by the communication interface, and
wherein the information processing apparatus includes a hardware processor and a communication interface.

9. A non-transitory computer-readable storage medium storing a program for causing a computer of a radiation image imaging apparatus, which generates an image from irradiated radiation, to perform functions comprising:
communicating directly by wireless communication with an information processing apparatus, which performs wireless communication, and receiving installation setting information transmitted from the information processing apparatus to perform a predetermined setting of the radiation image imaging apparatus at a time of an installation of the radiation image imaging apparatus; and
performing the predetermined setting of the radiation image imaging apparatus at the time of the installation of the radiation image imaging apparatus in accordance with the installation setting information received in the communicating,
wherein:
the program causes the computer to judge whether the predetermined setting of the radiation image imaging apparatus at the time of the installation of the radiation image imaging apparatus is completed when information is received from the information processing apparatus.

10. A radiation image imaging apparatus that generates an image from irradiated radiation, the radiation image imaging apparatus comprising:
a communication interface that directly communicates by wireless communication with an information processing apparatus, wherein the communication interface receives installation setting information transmitted from the information processing apparatus to perform a predetermined setting of the radiation image imaging apparatus at a time of an installation of the radiation image imaging apparatus; and
a hardware processor that performs the predetermined setting of the radiation image imaging apparatus at the time of the installation of the radiation image imaging apparatus in accordance with the installation setting information received by the communication interface,
wherein:
the radiation image imaging apparatus is provided with an access point function, whereby the radiation image imaging apparatus is operable as a parent device in wireless communication, and the information processing apparatus is operable as a child device in wireless communication with the radiation image imaging apparatus operating as the parent device, and the information processing apparatus comprises a hardware processor and a communication interface.

11. The radiation image imaging apparatus according to claim 10, wherein the hardware processor of the radiation image imaging apparatus judges whether the predetermined setting of the radiation image imaging apparatus at the time of the installation of the radiation image imaging apparatus is completed when information is received from the information processing apparatus by the communication interface.

12. The radiation image imaging apparatus according to claim 11, wherein the hardware processor of the radiation image imaging apparatus judges that the predetermined setting of the radiation image imaging apparatus at the time of the installation of the radiation image imaging apparatus is complete when a setting of all predetermined items is finished.

13. The radiation image imaging apparatus according to claim 11, wherein, when it is judged that the predetermined setting of the radiation image imaging apparatus at the time of the installation of the radiation image imaging apparatus is not completed, the hardware processor of the radiation image imaging apparatus judges whether the information received from the information processing apparatus is installation-related information related to the predetermined setting of the radiation image imaging apparatus at the time of the installation of the radiation image imaging apparatus, and when it is judged that the information is not the installation-related information, a wireless connection with the information processing apparatus is not permitted.

14. The radiation image imaging apparatus according to claim 11, wherein, when it is judged that the predetermined setting of the radiation image imaging apparatus at the time of the installation of the radiation image imaging apparatus is not completed, the hardware processor of the radiation image imaging apparatus judges whether the information processing apparatus, which transmitted the information, is a device in which the predetermined setting of the radiation image imaging apparatus at the time of the installation of the radiation image imaging apparatus is being executed, and when it is judged that the information processing apparatus is not the device in which the predetermined setting of the radiation image imaging apparatus at the time of the installation of the radiation image imaging apparatus is being executed, a wireless connection with the information processing apparatus is not permitted.

15. The radiation image imaging apparatus according to claim 10, wherein, after the predetermined setting of the radiation image imaging apparatus at the time of the installation of the radiation image imaging apparatus is completed, the hardware processor sets an operation mode of the radiation image imaging apparatus to one of a mode operating as the parent device, a mode operating as a child device with respect to another parent device, or a mode in which wireless communication is invalid according to the installation setting information transmitted from the information processing apparatus.

16. An electronic device, comprising:
a communication interface that directly communicates by wireless communication with an information processing apparatus, wherein the communication interface receives installation setting information transmitted from the information processing apparatus to perform a predetermined setting of the electronic device at a time of an installation of the electronic device; and
a hardware processor that performs the predetermined setting of the electronic device at the time of the installation of the electronic device in accordance with the installation setting information received by the communication interface,
wherein:
the electronic device is provided with an access point function, whereby the electronic device is operable as a parent device in wireless communication, and the information processing apparatus is operable as a child device in wireless communication with the electronic device operating as the parent device, and
the information processing apparatus comprises a hardware processor and a communication interface.

17. A wireless communication system comprising:
a radiation image imaging apparatus that generates an image from irradiated radiation; and
an information processing apparatus connectable to the radiation image imaging apparatus by wireless communication,
wherein the radiation image imaging apparatus includes:
a communication interface that directly communicates by wireless communication with the information processing apparatus, and receives installation setting information transmitted from the information processing apparatus to perform a predetermined setting of the radiation image imaging apparatus at a time of an installation of the radiation image imaging apparatus; and
a hardware processor that performs the predetermined setting of the radiation image imaging apparatus at the time of the installation of the radiation image imaging apparatus in accordance with the installation setting information received by the communication interface,
wherein the radiation image imaging apparatus is provided with an access point function, whereby the radiation image imaging apparatus is operable as a parent device in wireless communication, and the information processing apparatus is operable as a child device in wireless communication with the radiation image imaging apparatus operating as the parent device, and
wherein the information processing apparatus includes a hardware processor and a communication interface.

18. A non-transitory computer-readable storage medium storing a program for causing a computer of a radiation image imaging apparatus, which generates an image from irradiated radiation, to perform functions comprising:
communicating directly by wireless communication with an information processing apparatus, which performs wireless communication, and receiving installation setting information transmitted from the information processing apparatus to perform a predetermined setting of the radiation image imaging apparatus at a time of an installation of the radiation image imaging apparatus; and
performing the predetermined setting of the radiation image imaging apparatus at the time of the installation of the radiation image imaging apparatus in accordance with the installation setting information received in the communicating,
wherein:
the program causes the computer to execute an access point function, whereby the radiation image imaging apparatus is operable as a parent device in wireless communication, and the information processing apparatus is operable as a child device in wireless communication with the radiation image imaging apparatus operating as the parent device.

\* \* \* \* \*